United States Patent [19]

Vesley et al.

[11] 3,985,769

[45] Oct. 12, 1976

[54] ACETAL DERIVATIVES OF CYCLOOCTYL CARBOXALDEHYDES

[75] Inventors: Jerome A. Vesley, Park Ridge; Stephen N. Massie, Palatine, both of Ill.

[73] Assignee: Universal Oil Products Company, Des Plaines, Ill.

[22] Filed: Nov. 15, 1974

[21] Appl. No.: 524,167

[52] U.S. Cl. .............................. 260/338; 260/340.9; 260/598; 260/611 R; 252/522
[51] Int. Cl.$^2$ ......................................... C07D 317/00
[58] Field of Search ......... 252/522; 260/338, 340.9, 260/598, 611 R

[56] References Cited
UNITED STATES PATENTS

| | | | |
|---|---|---|---|
| 3,509,221 | 4/1970 | Falbe et al. | 260/598 |
| 3,514,489 | 5/1970 | Lemberg | 252/522 |
| 3,812,059 | 5/1974 | Rijke et al. | 252/522 |
| 3,847,975 | 11/1974 | Hall | 252/522 |

OTHER PUBLICATIONS

De Botton – Chem. Abs. 69, 26841 (1968).

*Primary Examiner*—C. Davis
*Attorney, Agent, or Firm*—James R. Hoatson, Jr.; Raymond H. Nelson; William H. Page, II

[57] ABSTRACT

Cyclooctyl carboxaldehydes and acetal derivatives thereof may be utilized as fragrant compositions, either alone or in admixture with other compounds.

5 Claims, No Drawings

ACETAL DERIVATIVES OF CYCLOOCTYL CARBOXALDEHYDES

This invention relates to oxygenated cyclic compounds and derivatives thereof which may be used as fragrant compositions. More specifically, the invention is concerned with cyclooctyl carboxaldehyde compounds which possess a desirable fragrance, and to their use as a component of fragrant compositions.

Heretofore, many of the compounds which are used in the aroma industry for the preparation of fragrances or aroma compositions which are added to cosmetics and toiletry articles such as perfumes, colognes, soaps, talcs, bath powders, pomades, etc., have been naturally occurring compounds or have been derived from naturally occurring vegetable sources such as flowers, including rose petals, geranium petals, or other petals which possess distinctive fragrances, roots, bushes, trees, etc., or animal sources such as the musk deer, civet, beaver, etc. However, the sources for these aroma chemicals are subject to the whims and vagaries of nature such as drought, floods, heat, unseasonable changes in climate, scarcity of game, etc. The aforementioned climatic conditions will insure either an abundant crop or in some instances insure a poor or sparse crop of the desired vegetable source. Therefore, the amount of these naturally occurring sources is, to a certain extent, uncertain and the compounders of the finished aroma compositions of matter cannot be assured of a constant supply to meet the demands and requirements of the industry. It is therefore necessary in order to insure a continued and certain supply of various aromatic compounds to synthesize compounds which possess the desired odor. By utilizing these synthetic compounds in place of naturally occurring compounds, it is possible to prepare aroma chemicals which possess identical odors and fragrances and which may be blended or used in formulations which are thereafter utilized in the perfume and soap industry for preparing the finished formulations of the type hereinbefore set forth. This is especially true in the preparation of perfumes which comprise a mixture of organic compounds which include, for example, alcohols, aldehydes, ketones, esters, hydrocarbons, etc., all of which are combined and fixed so that the odors of the finished compounds will produce a harmonious fragrance.

It has now been discovered that certain compounds comprising a cyclic oxygenated compound or derivative thereof and especially a cyclooctyl carboxaldehydic compound may be prepared and thereafter utilized in the addition of fragrant compositions which possess herbal, natural, floral, or green fragrances, the cyclooctyl carboxaldehydic compound itself possessing an intensely green odor.

It is therefore an object of this invention to provide a compound which possesses a desirable fragrance.

A further object of this invention is to provide a process for preparing compounds which possess desirable fragrances.

In one aspect an embodiment of this invention resides in a fragrant composition of matter containing, as one ingredient thereof, a cyclooctyl carboxaldehyde or an acetal derivative thereof.

A specific embodiment of this invention is found in a fragrant composition of matter possessing a floral fragrance containing, as one ingredient thereof, cyclooctyl carboxaldehyde.

Other objects and embodiments will be found in the following further detailed description of the present invention.

As hereinbefore set forth, the present invention is concerned with the use of a cyclic oxygenated compound, and more particularly, a cyclooctyl oxygenated compound as an ingredient or component in fragrant compositions. The desired compounds of the present invention which specifically include cyclooctyl carboxaldehyde and acetal derivatives thereof may be prepared in any suitable manner. For example, one method of preparing cyclooctyl carboxaldehyde is to treat cyclooctene or cyclooctadiene with carbon monoxide and hydrogen in the presence of a catalyst comprising dicobalt octacarbonyl. The preparation of cyclooctyl carboxaldehyde is effected at elevated temperatures and pressures, the operating parameters including a temperature in the range of from about 100° to about 250° C. or more and an elevated pressure ranging from about 100 to about 500 atmospheres or more. The aforesaid elevated pressures are afforded by combining the partial pressure of carbon monoxide and hydrogen, the ratio of hydrogen to carbon monoxide usually being in the range of from about one to about two atmospheres of hydrogen per atmosphere of carbon monoxide, although greater or lesser ratios may also be utilized. The cyclooctyl carboxaldehyde may be prepared in any suitable manner, either by batch or continuous type operation. For example, when a batch type operation is used, a quantity of the cyclooctene or cyclooctadiene is placed in an appropriate apparatus which may comprise a pressure-resistant vessel such as a rotating or mixing autoclave. In addition, the catalyst comprising dicobalt octacarbonyl is also added to the vessel, following which the vessel is sealed and the carbon monoxide and hydrogen are pressed in until the desired operating pressure is reached. Alternatively, the desired catalyst comprising dicobalt octacarbonyl can be prepared in situ by varying the operating conditions of the reaction within the hereinbefore set forth parameters. The vessel is then heated to the desired operating temperature within the range hereinbefore set forth and maintained at that range for a predetermined period of time which may range from about 0.5 up to about 20 hours or more in duration. Upon completion of the desired residence time, heating is discontinued, the vessel is allowed to return to room temperature and the excess pressure is discharged therefrom. The vessel is opened and the reaction mixture is recovered therefrom. After treatment of the reaction mixture by conventional means which will include washing, drying, fractional distillation under reduced pressure, etc., the desired product comprising cyclooctyl carboxaldehyde is recovered therefrom.

It is also contemplated within the scope of this invention that the compounds of the present invention may be prepared in a continuous manner of operation. When this type of operation is used, the desired quantity of the cyclooctene or cyclooctadiene is continuously charged to a reaction vessel containing the dicobalt octacarbonyl catalyst. The reaction vessel is maintained at the proper operating conditions of temperature and pressure, the latter being afforded by the continuous introduction of carbon monoxide and hydrogen. After a predetermined residence time has elapsed, the reactor effluent is continuously withdrawn and subjected to conventional means of separation whereby the desired cyclooctyl carboxaldehyde is recovered while any unreacted cyclooctene or cyclooctadiene is recycled to form a portion of the feed stock.

In the event that the desired compounds comprise acetal derivatives of cyclooctyl carboxaldehyde, it is possible to prepare these compounds by treating the cyclooctyl carboxaldehyde with an alcohol, either monohydric or polyhydric in nature, or lower alkyl ortho esters thereof, in the presence of an acid catalyst. Examples of mono-, polyhydroxy alcohols or esters thereof which may be reacted with the cyclooctyl carboxaldehyde will include monohydroxy alcohols containing from 1 to about 6 carbon atoms such as methanol, ethanol, propanol, isopropanol, n-butanol, t-butanol, n-pentanol, sec-pentanol, n-hexanol, sec-hexanol, etc., glycols such as ethylene glycol, propylene glycol, butylene glycol, amylene glycol, hexylene glycol, etc., or lower alkyl orthoformate esters such as trimethyl orthoformate, triethyl orthoformate, tri-n-propyl orthoformate, triisopropyl orthoformate, tri-n-butyl orthoformate, etc. The reaction between the aforementioned mono-, polyhydroxy compounds or esters and cyclooctyl carboxaldehyde is, as hereinbefore set forth, effected in the presence of an acid catalyst. Examples of acidic catalysts which may be employed to produce the desired compound will include sulfuric acid, hydrochloric acid, benzenesulfonic acid, methylsulfonic acid, ethylsulfonic acid, p-toluenesulfonic acid, chlorosulfonic acid, sodium bisulfate, sulfonated polystyrene resins, etc. The reaction is preferably effected in the presence of a substantially inert organic solvent such as benzene, toluene, the xylenes, n-pentane, n-hexane, n-heptane, cyclopentane, methylcyclopentane, cyclohexane, etc., the temperature at which the reaction is effected being that of from about ambient to about the reflux temperature of the particular solvent which is employed. It is also contemplated within the scope of this invention that the reaction may also be effected in the presence of molecular sieves. In any event, the water which is formed during the reaction is continuously withdrawn during the time of reaction which may vary from about 0.5 up to about 10 hours or more in duration.

Examples of acetal derivatives of cyclooctyl carboxaldehydes which may be prepared and utilized as fragrant compounds will include cyclooctyl carboxaldehyde dimethyl acetal, cyclooctyl carboxaldehyde diethyl acetal, cyclooctyl carboxaldehyde dipropyl acetal, cyclooctyl carboxaldehyde dibutyl acetal, cyclooctyl carboxaldehyde dipentyl acetal, cyclooctyl carboxaldehyde dihexyl acetal, cyclooctyl carboxaldehyde ethylene acetal, cyclooctyl carboxaldehyde propylene acetal, cyclooctyl carboxaldehyde butylene acetal, cyclooctyl carboxaldehyde amylene acetal, cyclooctyl carboxaldehyde hexylene acetal, etc.

As in the case of the method for the preparation of cyclooctyl carboxaldehyde, the acetal derivatives of cyclooctyl carboxaldehyde may also be prepared in either a batch or continuous type operation. For example, when a batch type operation is used, a quantity of the cyclooctyl carboxaldehyde and mono-, polyhydroxy compound or lower alkyl ester thereof, in stoichiometric or excess of stoichiometric concentrations is placed in an appropriate apparatus such as an alkylation flask which is provided with heating and refluxing means. The particular solvent which is to be employed is also added, and thereafter the flask is heated to the desired temperature while water is removed by any appropriate method. Upon completion of the desired residence time, which is within the range hereinbefore set forth, heating is discontinued and the reaction mixture is recovered. The desired acetal derivative is separated from any unreacted alcohols and cyclooctyl carboxaldehyde by conventional means of the type hereinbefore set forth and recovered. When the reaction between the cyclooctyl carboxaldehyde and the mono-, polyhydroxy compound or lower alkyl ester thereof is effected in a continuous manner, the starting materials are continuously charged to a reaction zone which is maintained at the proper operating conditions of temperature and pressure. The particular solvent which is to be employed in the reaction is also charged to the reaction zone through a separate line or, if so desired, it may be admixed with one or both of the starting materials and the resulting mixture charged thereto in a single stream. The reactor effluent is continuously withdrawn and subjected to conventional means of separation whereby the desired acetal derivative of the cyclooctyl carboxaldehyde is recovered while any unreacted starting materials and/or solvent are recycled to the reaction zone to form a portion of the feed stock.

The cyclooctyl carboxaldehyde or acetal derivative of the type hereinbefore set forth in greater detail may be present in the fragrant composition of matter in varying amounts ranging from about 0.5 up to about 20 or more parts by weight of the finished composition of matter.

The following examples are given to illustrate the process for preparing cyclooctyl carboxaldehyde and acetal derivatives thereof as well as finished fragrant compositions of matter. However, these examples are not intended to limit the generally broad scope of the present invention in strict accordance therewith.

EXAMPLE I

To illustrate a process for preparing cyclooctyl carboxaldehyde, 224 grams (2.0 mole) of cyclooctene was placed in the glass liner of a rotating autoclave. Following this 2 moles of dicobalt octacarbonyl in 20 ml of pentane was added to the autoclave immediately prior to sealing thereof. Following this, 60 atmospheres of carbon monoxide and 120 atmospheres of hydrogen were charged to the autoclave which was then heated to a temperature of 180° C. and maintained thereat for a period of 8 hours. At the end of the 8-hour period, heating was discontinued and the autoclave was allowed to cool to room temperature. The excess pressure was discharged and the autoclave was opened. The reaction product comprising an alcohol solution containing a small amount of water and black precipitated cobalt was decanted to remove the solid and the desired product comprising cyclooctyl carboxaldehyde was recovered therefrom.

EXAMPLE II

To prepare the acetal derivatives of cyclooctyl carboxaldehyde, a mole proportion of cyclooctyl carboxaldehyde which was prepared according to Example I above is placed in an alkylation flask along with a mole proportion of ethylene glycol. In addition, the flask will also contain a benzene solvent and a catalytic amount of sulfuric acid. The flask which is provided with refluxing means is then heated to the reflux temperature of benzene and maintained thereat for a period of 4 hours, the water of the reaction being continuously removed from the flask. At the end of the 4-hour period, heating is discontinued and after the reaction mixture has returned to room temperature, it is subjected to fractional distillation whereby the desired cyclooctyl carboxaldehyde ethylene acetal is recovered.

EXAMPLE III

In a manner similar to that set forth in Example II above, equimolar proportions of cyclooctyl carboxaldehyde and 2-methyl-2,4-pentanediol are placed in an alkylation flask along with a benzene solvent and a catalytic amount of p-toluenesulfonic acid. The flask is then heated to the reflux temperature of benzene and maintained thereat for a period of 4 hours, the water which is formed during the reaction being continuously removed therefrom. At the end of the 4-hour period, heating is discontinued and the reaction mixture is allowed to return to room temperature. The desired product comprising cyclooctyl carboxaldehyde hexylene acetal is recovered after subjecting the mixture to fractional distillation under reduced pressure.

EXAMPLE IV

In this example, one mole of cyclooctyl carboxaldehyde and four moles of ethyl alcohol in a benzene solvent and in the presence of a catalytic amount of sulfuric acid are heated at reflux for a period of 6 hours while the condensate is passed through a bed of molecular sieves prior to being returned to the reactor. The desired product comprising cyclooctyl carboxaldehyde diethyl acetal is recovered from the reaction mixture after subjecting the mixture to fractional distillation under reduced pressure.

EXAMPLE V

To an alkylation flask containing 300 grams of anhydrous methyl alcohol, 9.3 grams of a catalyst comprising a sulfonated resin known in the trade as Amberlyst 15, and 2.5 grams of butylated hydroxytoluene, was added 490 grams of cyclooctyl carboxaldehyde and 490 grams of trimethyl orthoformate. The mixture was stirred for a period of 15 hours at a temperature of 25° to 30° C. with stirring. At the end of the 15-hour period, the solution was filtered and 25 grams of soda ash was added, with stirring, to the filtrate. The solids were again removed by filtration and the filtrate was stripped of solvent. The crude oil which remained was subjected to fractional distillation under reduced pressure and the desired product comprising 400 grams of cyclooctyl carboxaldehyde dimethyl acetal which possessed a fruity, apple-like odor was recovered.

EXAMPLE VI

In this example a fragrant composition of matter which possesses a floral fragrance is prepared by admixing a specific combination of compounds according to the following recipe:

| Ingredient | Parts by Weight |
| --- | --- |
| n-octanal | 0.5 |
| n-decanal | 0.5 |
| resin Benzoin | 3.0 |
| resin Labdanum | 1.5 |
| Lavandin Oil | 15.5 |
| Polyalkylated acetyl tetralin | 1.5 |
| Nerol | 15.0 |
| Citral diethyl acetate | 30.0 |
| Orange Sweet Oil | 5.0 |
| Rosemary Oil | 3.0 |
| Cyclooctyl carboxaldehyde | 1.5 |
| Inert liquids | 23.0 |

EXAMPLE VII

Another example of a fragrant composite which will possess a fragrance of rose will comprise the following combination of ingredients according to the recipe:

| Ingredient | Parts By Weight |
| --- | --- |
| Citronellol | 45 |
| Citronellyl acetate | 6 |
| Benzophenone | 5 |
| Nerol | 10 |
| Linalool | 55 |
| Hydroxycitronellal | 10 |
| Phenylethyl alcohol | 3 |
| Phenylethyl dimethyl carbinol | 3 |
| Oil Bois de Rose | 8 |
| Isoeugenol | 0.5 |
| Oil Caraway | 0.5 |
| n-decanal | 0.5 |
| Isomenthol | 1.5 |
| Cyclooctyl carboxaldehyde dimethyl acetal | 1.0 |

In addition, other compounds such as the cyclooctyl carboxaldehyde ethylene acetal, cyclooctyl carboxaldehyde diethyl acetal, and cyclooctyl carboxaldehyde dibutyl acetal, when added to the above fragrant composite in place of the cyclooctyl carboxaldehyde dimethyl acetal, will also enhance the fragrance by adding a green note to said composite.

We claim as our invention:

1. An acetal derivative of cyclooctyl carboxaldehyde.
2. The compound of claim 1 being cyclooctyl carboxaldehyde ethylene acetal.
3. The compound of claim 1 being cyclooctyl carboxaldehyde hexylene acetal.
4. The compound of claim 1 being cyclooctyl carboxaldehyde diethyl acetal.
5. The compound of claim 1 in which said cyclooctyl carboxaldehyde dimethyl acetal.

* * * * *